United States Patent
Reitinger et al.

(10) Patent No.: US 10,401,160 B2
(45) Date of Patent: Sep. 3, 2019

(54) METHOD FOR DETERMINING THE LAYER THICKNESS OF A CONNECTING LAYER BETWEEN TWO PACKAGING LAYERS

(71) Applicants: CONSTANTIA TEICH GMBH, Weinburg (AT); RESEARCH CENTER FOR NON DESTRUCTIVE TESTING GMBH, Linz (AT)

(72) Inventors: Bernhard Reitinger, Alkoven (AT); Saeid Zamiri, Linz (AT); Clemens Gruensteidl, Linz (AT); Juergen Roither, Grieskirchen (AT); Martin Kornfeld, Klosterneuburg (AT); Alfred Wegenberger, Langenlois (AT)

(73) Assignees: CONSTANTIA TEICH GMBH, Weinburg (AT); RESEARCH CENTER FOR NON DESTRUCTIVE TESTING GMBH, Linz (AT)

( * ) Notice: Subject to any disclaimer, the term of this patent is extended or adjusted under 35 U.S.C. 154(b) by 215 days.

(21) Appl. No.: 14/781,958

(22) PCT Filed: Mar. 12, 2014

(86) PCT No.: PCT/EP2014/054773
§ 371 (c)(1),
(2) Date: Oct. 2, 2015

(87) PCT Pub. No.: WO2014/161706
PCT Pub. Date: Oct. 9, 2014

(65) Prior Publication Data
US 2016/0054122 A1 Feb. 25, 2016

(30) Foreign Application Priority Data
Apr. 4, 2013 (AT) .............. A 50229/2013

(51) Int. Cl.
*G01B 17/02* (2006.01)
*G01B 11/06* (2006.01)
*G01N 29/07* (2006.01)

(52) U.S. Cl.
CPC .............. *G01B 17/02* (2013.01); *G01B 11/06* (2013.01); *G01B 11/0666* (2013.01);
(Continued)

(58) Field of Classification Search
CPC .... G01B 11/06; G01B 11/0666; G01B 17/02; G01N 29/07; G01N 2291/02854; G01N 2291/011
See application file for complete search history.

(56) References Cited

U.S. PATENT DOCUMENTS 4,710,030 A * 12/1987 Tauc ................. G01N 21/1702
356/432
5,038,615 A * 8/1991 Trulson ................ G01B 17/025
367/100

(Continued)

FOREIGN PATENT DOCUMENTS

| CA | 2 314 305 | 1/2002 |
|---|---|---|
| DE | 10 2011 089 475 | 6/2012 |
| WO | 2012/085131 | 6/2012 |

OTHER PUBLICATIONS

Canumalla et al., Metrology of Thin Layers in IC Packages using an Acoustic Microprobe: Bondline Thickness, 1999 IEEE, see attached publication.*

(Continued)

*Primary Examiner* — Xin Y Zhong
(74) *Attorney, Agent, or Firm* — Greenblum & Bernstein, P.L.C.

(57) ABSTRACT

For a simple, fast, safe and reliable determination of the layer thickness of a bonding layer between two layers of a packaging, a laser ultrasonic method is provided, in which the transit time of the ultrasonic wave through the first and second packaging layers (2, 3) is determined in advance, and a maximum ($M_1$, $M_2$, $M_n$) in the measurement signal (S) is sought, and the point in time of occurrence of this maximum ($M_1$, $M_2$, $M_n$) is determined as the total transit time ($T_1$, $T_2$, $T_n$) of the ultrasonic wave, and the transit time of the (Continued)

Figure 1:
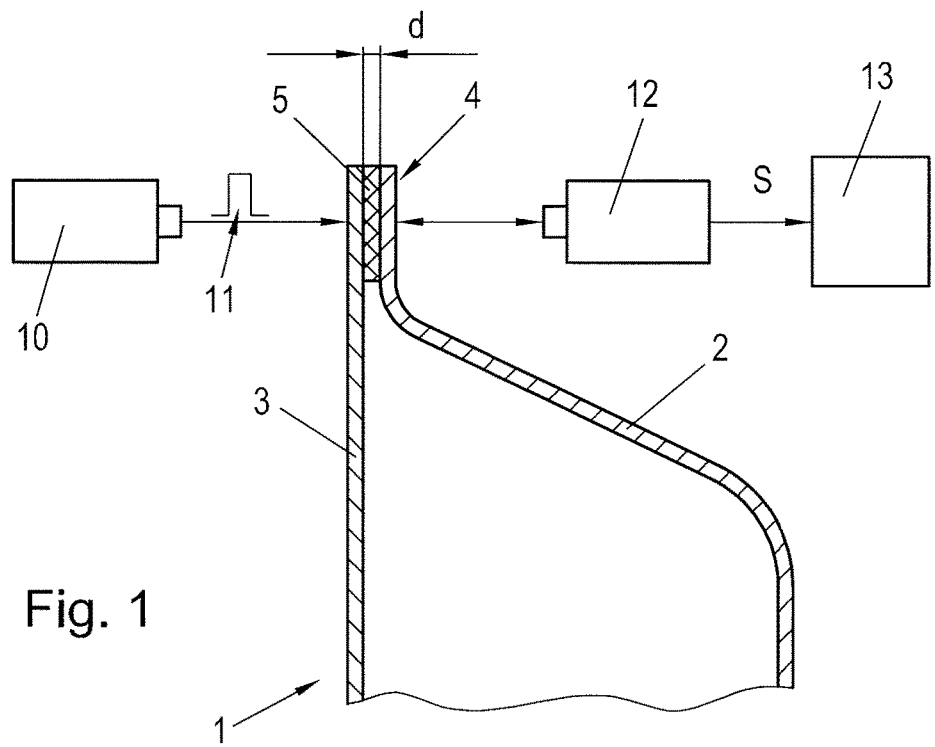

ultrasonic wave through the first and second packaging layers (2, 3) is subtracted from the total transit time ($T_1$, $T_2$, $T_n$), and the thickness (d) of the bonding layer is deduced from the known ultrasonic speed ($v_S$) in the bonding layer (5).

7 Claims, 3 Drawing Sheets

(52) U.S. Cl.
CPC ....... *G01N 29/07* (2013.01); *G01N 2291/011* (2013.01); *G01N 2291/02854* (2013.01)

(56) References Cited

U.S. PATENT DOCUMENTS

| | | | |
|---|---|---|---|
| 5,866,819 A | 2/1999 | Albu et al. | |
| 5,974,886 A * | 11/1999 | Carroll | G01B 17/025 73/1.82 |
| 2002/0134159 A1 | 9/2002 | He | |
| 2004/0085550 A1 | 5/2004 | Okuno et al. | |
| 2008/0021673 A1 * | 1/2008 | Blander | G01B 17/02 702/171 |
| 2010/0058824 A1 * | 3/2010 | Iwamoto | B21B 38/04 72/31.07 |
| 2013/0269438 A1 | 10/2013 | Hepp | |

OTHER PUBLICATIONS

Austrian Search Report conducted in counterpart Austrian Appln. No. A 50229/2013 (dated Feb. 17, 2014).

Int'l Search Report (PCT ISA/210) conducted in PCT/EP2014/054773, of which this Appln. is a U.S. National Stage (dated Apr. 11, 2014).

Written Opinion of Int'l Search. Auth., (PCT/IB/237) conducted in PCT/EP2014/054773, of which this Appln. is a U.S. National Stage (dated Oct. 6, 2015).

\* cited by examiner

METHOD FOR DETERMINING THE LAYER THICKNESS OF A CONNECTING LAYER BETWEEN TWO PACKAGING LAYERS

The present invention relates to a method for determining the layer thickness of a bonding layer between a first packaging layer and a second packaging layer, wherein the first layer is acted upon by a laser pulse and the resulting ultrasonic wave is detected on a surface of the first or second packaging layer, and the measurement signal, detected over time, is evaluated to determine the thickness of the bonding layer.

Packaging for foods or animal feed today often consists of containers, for example of aluminum or a plastic laminate, and a cover film made of plastic, aluminum, paper or a laminate thereof, for example for sealing the container. Alternatively, bags can also be produced from a film or a film laminate material and sealed by a seam after being filled. A sealing process, for example a heat sealing process or an ultrasonic sealing process, or an adhesive bonding process is often used for the sealing. A sealing medium such as polyethylene, polypropylene and/or copolymers thereof is applied, for example by a coextrusion process to both the container and also the cover film and/or to both sheets of film. In the case of adhesive bonding, it is sufficient if an adhesive is applied to only one portion, and naturally the adhesive can also be applied to both portions.

In contrast with the thicknesses of the cover film and of the container, which can be kept in a narrow tolerance range during the manufacturing process and is thus more or less constant, the resulting thickness of the sealing layer or adhesive layer is subject to great fluctuations due to the process. Therefore, in manufacturing such packaging containers, the thickness of the sealing layer or the adhesive layer must be monitored continuously as part of quality assurance. This is currently accomplished by means of a mechanical gauge, for example. To do so, however, the sample must first be etched by using an acid to expose the layer to be measured and to enable measurement of the thickness of the sealing layer and/or the adhesive layer. However, such methods are complex, because it is necessary to work with acid and great safety measures must be taken and observed with regard to occupational safety. Furthermore, this method is time consuming because, on the one hand, the working steps require time and, on the other hand, a great deal of manual labor is involved. The layer thickness can also be determined by means of computer-assisted tomography, but that is expensive due to the cost of the equipment.

In addition, there are also known noncontact methods based on laser ultrasonic spectroscopy. For these methods, a sample is treated with a short laser pulse and thus with a broad frequency spectrum. A propagating ultrasonic wave is created in the sample due to a thermoelastic heating and/or ablation of the surface of the sample, and this is also detected in a noncontact process, for example by means of an interference method, for example using a laser Doppler vibrometer. Detection can be performed in the vicinity of the excitation or on an opposing surface of the sample. By evaluating the frequency spectrum of the detected signal, it is possible to deduce certain properties of the sample, for example, its layer thickness. Such a method is described in CA 2 314 305 A1 for a multilayer sample, for example. This requires a model that describes the behavior of the multilayer sample and includes at least one parameter that is sought, such as the thickness of a layer for example, which influences the resonant frequency. The at least one parameter is then varied by using a best fit method to obtain the best possible correspondence of the resonant frequencies predicted by the model with the frequencies actually measured. The quality of this method definitely depends on the model of the sample, with a suitable model being required for each sample and therefore a very great effort being required. In addition, the method also involves a very high computational effort, in particular when several parameters are unknown and are to be determined. In the case of multiple unknown parameters, the uncertainty of the measurement method also increases and, along with that, the standard deviation of each parameter to be fitted also increases.

One object of the present invention was therefore to determine the layer thickness of a bonding layer between two layers of a packaging by a simple, safe, fast and reliable method.

This object is achieved according to the invention by determining the transit time of the ultrasonic wave through the first and second layers of packaging in advance, and by searching a maximum in the measurement signal and the point in time of occurrence of this maximum is determined as the total transit time of the ultrasonic wave, and then the transit time of the ultrasonic wave through the first and second packaging layers is subtracted from the total transit time, and the thickness of the bonding layer is deduced from the known ultrasonic velocity in the bonding layer. By using available a priori knowledge, the thickness of the bonding layer can be determined in a very simple and rapid manner without having to perform complex signal analyses and calculations. This also allows measurements to be performed on a great many measurement points in a short period of time.

The search for the maximum can take place by cross-correlation with a known signal pattern in a first method or by means of a priori knowledge in a second method, when a time window is defined in the range of the total transit time and the maximum is sought within this time window.

Without a priori knowledge, the search for the first local maximum may be conducted in a third method by analyzing the noise in the spectrum and the noise power in the measurement signal before the first signal arrival to be expected in order to find a threshold value in the amplitude and rise time. With the help of these threshold values, the first local maximum can be determined. This third method includes certain error sources, such as voltage peaks, which are caused by high-frequency scattering, for example, and can be misinterpreted, but it has the great advantage of allowing a search for a maximum without a priori knowledge.

To compensate for statistical fluctuations in measured values, it is possible to provide for a plurality of individual measurements to be performed within a measurement grid and for averages to be formed over these individual measurements to determine the thickness of the bonding layer. The required individual measurements can be performed in a very short period of time by means of the measurement method according to the invention.

To be able to correctly detect regions of a different surface structure, for example embossing in a packaging layer, a histogram of the respective transit times can be prepared from the maximums determined from the individual measurements and then can be used to ascertain regions of a different surface structure. The thickness of the bonding layer can then be determined from this graph for at least one surface structure detected.

Figure 3:
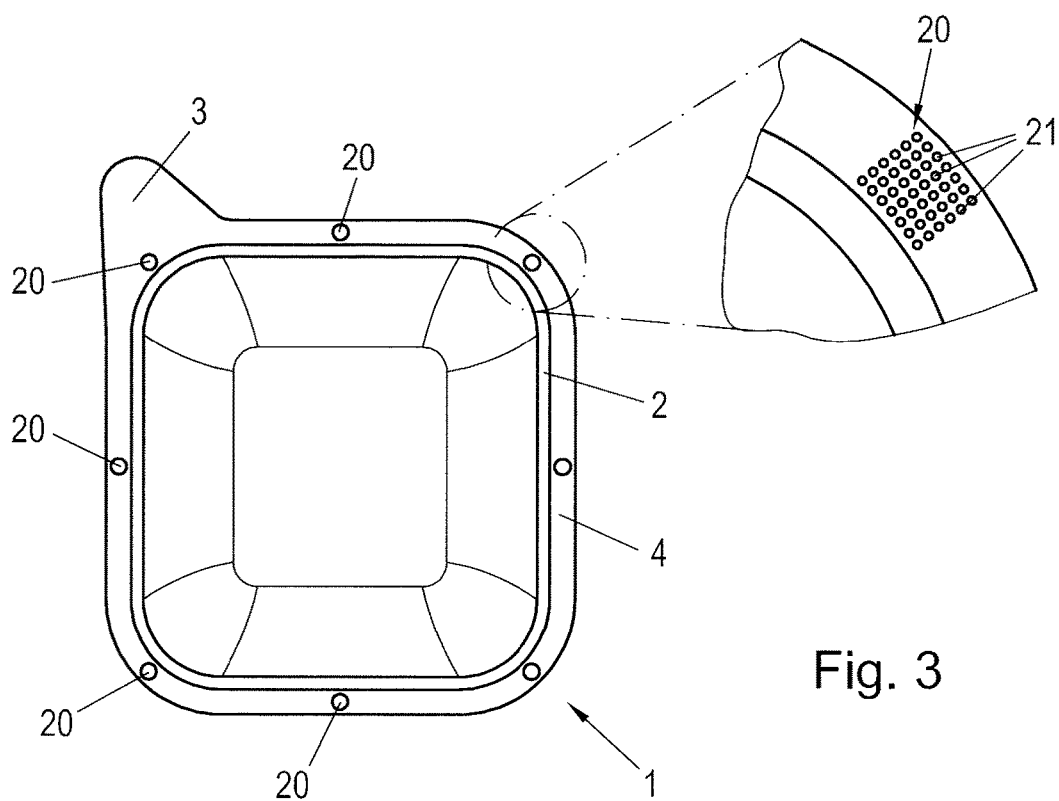
Figure 2:
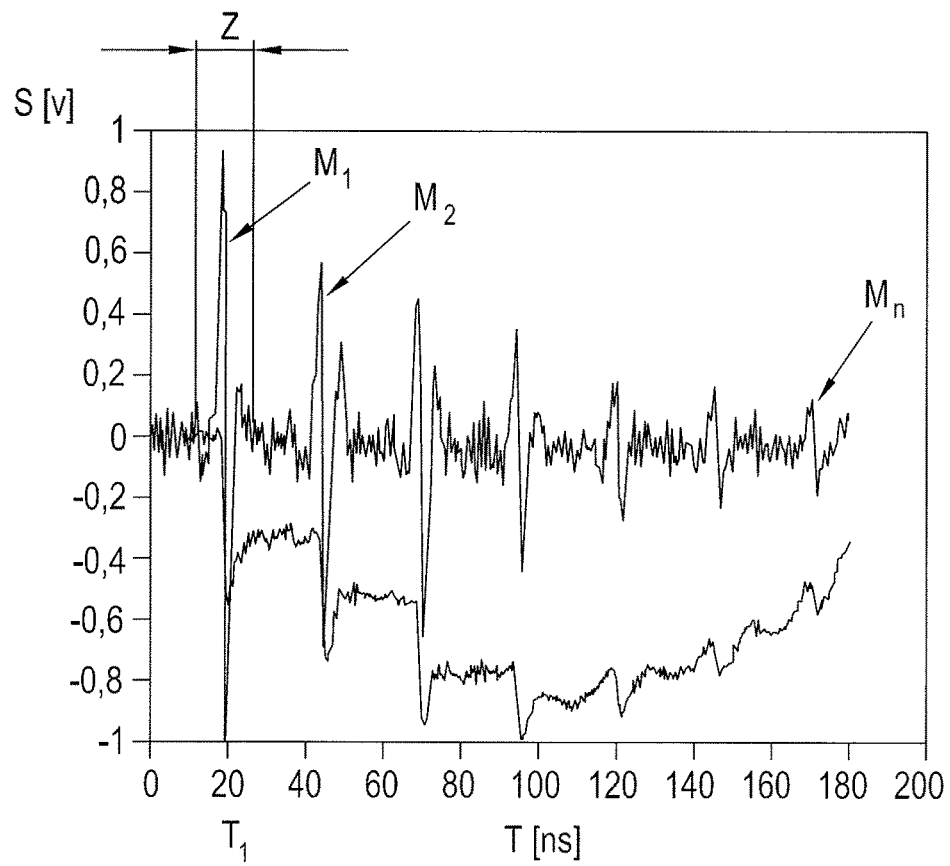
Figure 4:
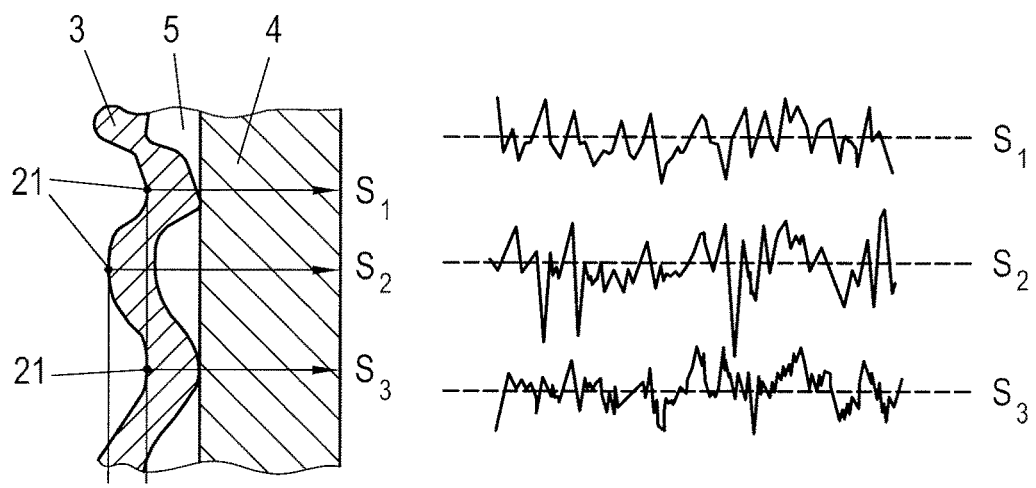
Figure 5:
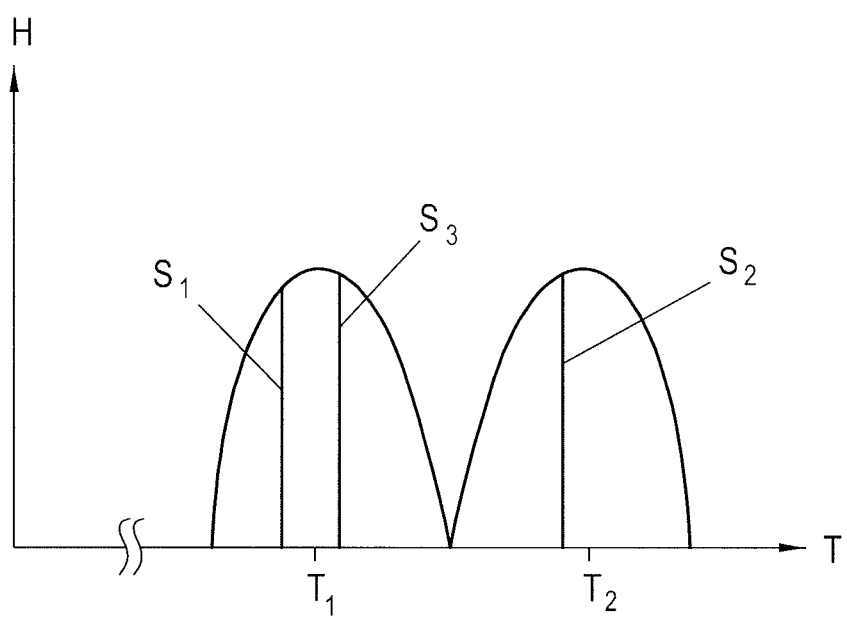

The present invention is explained in greater detail below with reference to FIGS. 1 through 5, which show advantageous embodiments of the invention in an exemplary, schematic and nonrestrictive form, showing:

FIG. 1 a schematic measurement arrangement according to the invention,

FIG. 2 a recorded measurement signal of the ultrasonic wave generated,

FIG. 3 the measurement at various measurement locations, each with a plurality of measurement points, and FIGS. 4 and 5 the measurement and evaluation on a structured packaging layer.

FIG. 1 shows schematically and in greatly simplified form a setup for determining the thickness of a bonding layer on a package 1. The package consists of a first packaging layer 2, for example a container, such as a dish, and a second packaging layer 3, for example a cover film. A bordering region 4 is provided here on a peripheral border of the first packaging layer 2, so that the second packaging layer 3 can be attached to the first packaging layer 2 at this border.

However, the package could of course also be embodied in the form of a bag or something similar, connected to one another in the region of a connecting seam. The first packaging layer 2 may be produced, for example from paper, aluminum or a plastic or a laminate of these materials in the form of a multilayer film. The second packaging layer 3 may be produced from paper, aluminum or a plastic or a laminate of these materials in the form of a multilayer film. The first and/or second packaging layer 2, 3 may also be printed on one side, preferably the free visible surface, and/or may be metallized on one side, preferably the side facing the interior of the package 1.

A bonding layer 5, for example a sealing layer or an adhesive layer, is provided for bonding the two packaging layers 2, 3. To measure the thickness d of the bonding layer 5, one side of the second packaging layer 3 is excited with an excitation laser 10 by means of a short laser pulse 11, preferably with a pulse duration of <1 ns. Due to the short laser pulse 11, a broadband ultrasonic wave is generated in the package, which propagates in the package 1. After passing through the second packaging layer 3, the bonding layer 5 and the first packaging layer 2, this ultrasonic wave is detected on the surface of the first packaging layer 2, i.e. opposite the excitation, using a detector 12. However, the detector 12 may also be arranged so that it detects the reflected ultrasonic wave on the surface of the second packaging layer 3, i.e. on the same side as the excitation.

The detector 12 may be embodied as an interferometer, for example as a known Fabry-Perot interferometer, as a homodyne or heterodyne Michelson or Mach-Zehnder interferometer, as a photorefractive interferometer or the like. Using this interferometer, the vibration of the surface of the first or second packaging layers 2, 3 induced by the ultrasonic wave is sensed and detected. The design, the components and the function of such interferometers have long been adequately well known, so that they need not be discussed in detail here. The detector 12 supplies a measurement signal S to an evaluation unit 13.

The measurement signal S recorded in this way is depicted in FIG. 2, for example, where the lower curve corresponds to the crude signal and the upper curve corresponds to the crude signal that has been filtered and/or processed in a band pass filter, for example. One can recognize in the measurement signal S distinct maxima $M_n$, namely a first maximum $M_1$ after approx. 20 ns and other following, attenuated maxima $M_2$, $M_n$, which are caused by the echo of the ultrasonic wave in the packaging 1. To determine the thickness d of the bonding layer 5, the transit times T of these maxima $M_n$ are evaluated. The first maximum $M_1$ with the strongest signal is preferably used, but any other maximum may also be used.

To do so, the transit times of the ultrasonic wave in the first and second packaging layers 2, 3 are determined in advance. This is done by means of reference measurements or by calculation from the known physical properties of the material. It is then known how long the ultrasonic wave needs to pass through the packaging layers 2, 3. Since the packaging layers can be produced with a very high precision and constancy with regard to the thickness as well as the properties of the material, they can therefore be assumed to be more or less constant. The total transit time $T_1$ of the ultrasonic wave through the packaging 1 must therefore be determined at the location to be measured.

Therefore, the point in time of occurrence of a maximum M, preferably the first maximum $M_1$, is sought in the measurement signal S that corresponds to the total transit time $T_1$ of the ultrasonic wave through the packaging 1.

Known methods are recommended for the search for the maximum such as, for example, cross-correlation with known signal patterns (state of the art in radar applications, GPS, ultrasound, etc.), a search for the maximum within certain limits or a search for the first local maximum by analyzing the noise in the spectrum and the noise power in the measurement signal S before the expected arrival of the first signal in order to find a threshold value in the amplitude and rise time. With the help of these threshold values, the first local maximums can be determined without a priori knowledge of the measurement signal S.

The known transit times $T_2$, $T_3$ of the first and second packaging layers 2, 3 are subtracted from the total transit time $T_1$, so that the transit time $T_S$ through the bonding layer 5 remains. Then the thickness d of the bonding layer 5 can be deduced from this transit time $T_S$. The propagation speed $v_S$ of the ultrasonic wave through the material of the bonding layer 5 is either known or can be determined from reference measurements. The thickness d of the bonding layer 5 can then be calculated directly from the determined transit time $T_S$, for example, in the form $d=T_S \cdot v_S$, where $T_S=T_1-T_2-T_3$. In other words, to determine the thickness d of the bonding layer 5, a priori knowledge about the packaging 1 is relied on.

However, this a priori knowledge may also be used to simplify the search for the maximum and thus to accelerate the determination of the thickness d of the bonding layer 5. For example, a time window Z within which the occurrence of a maximum is to be expected (see FIG. 2) can be defined on the basis of the transit times $T_2$, $T_3$ in the first and second packaging layers 2, 3, which can be regarded as known, see FIG. 2, and the search for a maximum, for example by means of cross-correlation, can then be limited to this time window Z. Since the approximate thickness d of the bonding layer 5 and/or a range of the possible thickness d is known from the production process, the time window Z can be determined easily. The search for the maximum can then be limited to this time window Z.

Without a priori knowledge, the search for the first local maximum may take place by analyzing the noise in the spectrum and the noise power in the measurement signal before the first signal arrival to be expected (see FIG. 2, t<10 ns), in order to find a threshold value in the amplitude and rise time. The first local maximums $M_1$ can be determined with the help of these threshold values.

An improvement in the evaluation can also be achieved if the determination of the thickness d of the bonding layer 5 is not made on the basis of a single measurement but instead is made on the basis of a plurality of measurements, as shown in FIG. 3. In the range of the bonding layer 5, i.e., here in the bordering region 4 of the container of the package 1, for example, a number of measurement regions 20, for example a region of 1.5 mm×1.5 mm each, is defined. Several measurement points 21 are provided in each measurement range and are arranged in a measurement grid with a distance of 50 μm between the measurement points 21, for example. The local thickness of the bonding layer 5 is determined at each measurement point 21, and the individual local thicknesses are then averaged to determine the thickness d of the bonding layer 5 for the respective measurement region 20.

To do so, it is possible to provide that the package 1 is arranged movably in a plane normal to the excitation laser beam, for example being clamped on a carriage movable in this plane by means of driven linear guides. The packaging 1 is then positioned accordingly for the individual measurements by means of a suitable control, for example being integrated into the evaluation unit 13. Alternatively or additionally, the excitation laser 10 and the detector 12 may also be arranged movably. Based on the use of high-energy lasers, the device must of course also satisfy the safety provisions that are provided.

It is also possible that a packaging layer 3 has a surface structure, for example an embossing, as represented in FIG. 4. Based on this surface structure, the local thicknesses d of the bonding layer 5 may fluctuate. By averaging as described above, a false thickness d of the bonding layer 5 would then result. To prevent this, the total transit times $T_1$ (or the transit time $T_S$ through the bonding layer 5) are plotted in a histogram from the individual measurements at the measurement points 21, as depicted in FIG. 5. To do so, as is well known, intervals of the total transit times $T_1$ are determined and the frequency H is determined, indicating how many measurements fall in the respective intervals. Then regions of different surface structure can be determined from the histogram, a range of transit times belonging to each region. Either an average transit time $T_{11}$, $T_{12}$ for each region is determined from this and then the thickness d of the bonding layer 5 for the regions of different surface structure can be determined from this, or the individual measurements are assigned to different regions and then an average value is determined as described above.

The invention claimed is:

1. A method for determining the layer thickness of a bonding layer between a first packaging layer and a second packaging layer, the method comprising:
    acting on the first packaging layer with a laser pulse, resulting in an ultrasonic wave at a surface of the first and second packaging layers;
    detecting the resulting ultrasonic wave at the surface of one of the first or second packaging layer; and
    evaluating a measurement signal, which is detected over time, for determining the bonding layer thickness, wherein a predetermined transit time of the ultrasonic wave through the first and second packaging layers is known prior to the evaluating of the measurement signal, the evaluation of the measurement signal comprising:
        looking for an occurrence of a maximum in the measurement signal;
        determining, from a point in time of a found occurrence of the maximum found in the measurement signal, the total transit time of the ultrasonic wave;
        subtracting the predetermined transit time of the ultrasonic wave through the first and second packaging layers from the total transit time; and
        deducing, from a known ultrasonic speed in the bonding layer, the thickness of the bonding layer.

2. The method according to claim 1, wherein the evaluating further comprises defining a time window in a range of the total transit time within which the looking for the maximum occurs.

3. The method according to claim 1, wherein the maximum is determined by cross-correlation with a known signal pattern.

4. The method according to claim 1, wherein the noise in the spectrum and the noise power are analyzed in the measurement signal before the first expected signal arrival, in order to find a threshold value in the amplitude and rise time as an indication of the maximum.

5. The method according to claim 1, wherein the evaluating of the measurement signal further comprises: performing a plurality of individual measurements within a measurement region and averaging the plurality of individual measurements to determine the bonding layer thickness.

6. The method according to claim 5, wherein regions of a different surface structure are determined from a histogram of respective total transit times of the plurality of individual measurements prepared from respective found maxima of the individual measurements, whereby a thickness for at least one surface structure is ascertained.

7. A method for determining the layer thickness of a bonding layer between a first packaging layer and a second packaging layer, the method comprising:
    acting on the first packaging layer with a laser pulse, resulting in an ultrasonic wave at a surface of the first and second packaging layers;
    detecting the resulting ultrasonic wave at the surface of one of the first or second packaging layer; and
    evaluating a measurement signal, which is detected over time, for determining the bonding layer thickness, wherein a predetermined transit time of the ultrasonic wave through the first and second packaging layers is known prior to the evaluating of the measurement signal, the evaluation of the measurement signal comprising:
        looking for an occurrence of a maximum in the measurement signal;
        determining, from a point in time of a found occurrence of the maximum found in the measurement signal, the total transit time of the ultrasonic wave;
        subtracting the predetermined transit time of the ultrasonic wave through the first and second packaging layers from the total transit time; and
        deducing, from a known ultrasonic speed in the bonding layer, the thickness of the bonding layer,
    wherein the evaluating of the measurement signal further comprises: performing a plurality of individual measurements within a measurement region, and
    wherein regions of a different surface structure are determined from a histogram of respective total transit times of the plurality of individual measurements prepared from respective found maxima of the individual measurements, whereby a thickness for at least one surface structure is ascertained.

* * * * *